(12) United States Patent
Grabowski et al.

(10) Patent No.: US 8,187,313 B2
(45) Date of Patent: May 29, 2012

(54) BIFURCATION CATHETER ASSEMBLY SIDE CATHETER BRANCH CONSTRUCTION AND METHODS

(75) Inventors: Gerald Grabowski, Plymouth, MN (US); Rob Lucas, Princeton, MN (US); Adam Jennings, Buffalo, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 348 days.

(21) Appl. No.: 12/184,487

(22) Filed: Aug. 1, 2008

(65) Prior Publication Data

US 2010/0030317 A1 Feb. 4, 2010

(51) Int. Cl.
*A61F 2/06* (2006.01)

(52) U.S. Cl. ...................... 623/1.11; 623/1.35

(58) Field of Classification Search .................. 623/1.11, 623/1.12; 606/191, 194; 604/101.01, 101.05
See application file for complete search history.

(56) References Cited

U.S. PATENT DOCUMENTS

| | | | |
|---|---|---|---|
| 5,591,172 A * | 1/1997 | Bachmann et al. | 623/1.11 |
| 6,203,568 B1 * | 3/2001 | Lombardi et al. | 623/1.13 |
| 6,210,429 B1 | 4/2001 | Vardi et al. | |
| 6,325,826 B1 | 12/2001 | Vardi et al. | |
| 6,692,483 B2 | 2/2004 | Vardi et al. | |
| 6,706,062 B2 | 3/2004 | Vardi et al. | |
| 7,220,275 B2 | 5/2007 | Davidson et al. | |
| 7,344,557 B2 * | 3/2008 | Yadin | 623/1.11 |
| 7,842,081 B2 * | 11/2010 | Yadin | 623/1.35 |
| 8,043,366 B2 * | 10/2011 | Brown et al. | 623/1.35 |
| 2004/0176837 A1 | 9/2004 | Atladottir et al. | |
| 2005/0149166 A1 * | 7/2005 | Schaeffer et al. | 623/1.13 |
| 2005/0251195 A1 | 11/2005 | Wang | |
| 2005/0273149 A1 | 12/2005 | Tran et al. | |
| 2005/0278010 A1 * | 12/2005 | Richardson | 623/1.11 |
| 2006/0229697 A1 * | 10/2006 | Gerdts et al. | 623/1.11 |
| 2007/0055132 A1 * | 3/2007 | Camus et al. | 600/407 |
| 2007/0203562 A1 | 8/2007 | Malewicz et al. | |
| 2008/0269866 A1 * | 10/2008 | Hamer et al. | 623/1.11 |
| 2010/0023107 A1 * | 1/2010 | Grabowski et al. | 623/1.11 |
| 2010/0030143 A1 * | 2/2010 | Anderson et al. | 604/103.07 |

FOREIGN PATENT DOCUMENTS

| | | |
|---|---|---|
| WO | 2005041810 | 5/2005 |
| WO | 2006036263 | 4/2006 |
| WO | 2007136637 | 11/2007 |
| WO | 2009029674 | 3/2009 |

* cited by examiner

*Primary Examiner* — Gary Jackson
*Assistant Examiner* — Amy Shipley
(74) *Attorney, Agent, or Firm* — Seager, Tufte & Wickhem, LLC

(57) ABSTRACT

A catheter assembly includes a main catheter branch and a side catheter branch. The main catheter branch includes a main balloon and a side balloon. The side catheter branch includes a transparent portion along at least a portion of a length of the side catheter branch. The transparent portion of the side catheter branch permits viewing of the side balloon through the transparent portion for alignment of the side balloon relative to the side catheter branch. The catheter assembly can further include a stent, wherein the stent includes a lateral branch opening. The transparent portion of the side catheter branch can also provide viewing of the side balloon through the side catheter branch to help align the side balloon with the lateral branch opening.

18 Claims, 6 Drawing Sheets

FIG. 10 FIG. 11 FIG. 12 FIG. 13

BIFURCATION CATHETER ASSEMBLY SIDE CATHETER BRANCH CONSTRUCTION AND METHODS

TECHNICAL FIELD

This disclosure relates to catheter assemblies for use in treating vessel bifurcations, and methods for assembling such catheter assemblies.

BACKGROUND

Catheters are used with stents and inflatable structures to treat conditions such as strictures, stenoses, and narrowing in various parts of the body. Various catheter designs have been developed for the dilatation of stenoses and to deliver and deploy stents at treatment sites within the body.

Stents are typically intraluminally placed by a catheter within a vein, artery, or other tubular shaped body organ for treating conditions such as, for example, occlusions, stenoses, aneurysms, dissections, or weakened, diseased, or abnormally dilated vessels or vessel walls, by expanding the vessels or by reinforcing the vessel walls. Once delivered, the stents can be expanded using one or more inflatable members such as balloons. Stents can improve angioplasty results by preventing elastic recoil and remodeling of the vessel wall and treating dissections in blood vessel walls caused by balloon angioplasty of coronary arteries. Stents can also be used as a drug delivery medium for treatment of damaged portions of a vessel.

While conventional stent technology is relatively well developed, stent technologies related to treatment of the region of a vessel bifurcation are still being developed.

SUMMARY OF THE DISCLOSURE

The present disclosure generally relates to catheter assemblies for treatment of vessel bifurcations. Although alternatives are possible, an example catheter assembly generally includes a main catheter branch and a side catheter branch. The main catheter branch includes a main balloon and a side balloon. The side balloon is configured to extend radially outward relative to the main balloon when the side balloon is inflated. The side catheter branch typically defines a branch guidewire lumen sized to advance over a branch guidewire. The side catheter branch can be aligned with the side balloon when the catheter assembly is assembled prior to treatment of the vessel bifurcation. At least a portion of the side catheter branch that is aligned with the side balloon can comprise a transparent material that permits viewing of the side balloon through the transparent portion of the side catheter branch. Viewing the side balloon through at least a portion of the side catheter branch can also promote alignment of the side balloon with a lateral branch opening of a stent when assembling the main and side catheter branches with the stent prior to use of the catheter assembly to treat a vessel bifurcation.

There is no requirement that an arrangement or method include all features characterized herein to obtain some advantage according to this disclosure.

DETAILED DESCRIPTION

This disclosure relates to bifurcation treatment systems, catheter assemblies, and related methods of treating bifurcations in a patient's body. The term bifurcation means a division location from one unit into two or more units. Generally, two types of bifurcations of a body organ include: 1) a main tubular member defining a main lumen and a branch tubular member defining a branch lumen that extends or branches off from the main tubular member, wherein the main and branch lumens are in fluid communication with each other, and 2) a primary or main member defining a primary or main lumen (also referred to as a parent lumen) that splits into first and second branch members defining first and second branch lumens. The term lumen means the cavity or bore of a tubular structure such as a tubular organ (e.g., a blood vessel).

An example bifurcation is a vessel bifurcation that includes a continuous main vessel and a branch vessel, wherein the vessels define a main lumen and a branch lumen, respectively that are in fluid communication with each other. Alternatively, a vessel bifurcation can include a parent vessel that divides into first and second branch vessels, wherein the vessels define a parent lumen and first and second branch lumens, respectively, which lumens are all in fluid communication with each other.

Example applications of the inventive principles disclosed herein include cardiac, coronary, renal, peripheral vascular, gastrointestinal, pulmonary, urinary, and neurovascular systems. The catheter assemblies, systems and methods disclosed herein can be used for locating a branch vessel of the vessel bifurcation and for placement of a stent relative to the vessel bifurcation for treatment of the vessel bifurcation.

While alternatives are possible, the example catheter assemblies disclosed herein generally include at a distal end portion thereof a main catheter branch and a side catheter branch. A stent can be mounted to or otherwise disposed about the main and side catheter branches for delivery to a vessel bifurcation treatment site. A distal end portion of the side catheter branch is configured to extend through a lateral branch opening of the stent and into a branch vessel at the vessel bifurcation. The side catheter branch can be used to align the lateral branch opening of the stent with an opening into the branch vessel. The side catheter branch typically comprises a material composition that is non-transparent so the assembler can see the side catheter branch for improved ease is handling the relatively small side catheter branch.

The main catheter branch can include a catheter shaft, a main balloon and a side balloon. When assembling the main and side catheter branches with the stent prior to treating the vessel bifurcation, the side balloon is positioned internal the stent in axial and radial alignment with the lateral branch opening of the stent. The side catheter branch extends into a proximal open end of the stent and out of the stent through the lateral branch opening. The stent is then secured to the main and side catheter branches using, for example, a crimping technique.

Maintaining the side balloon in alignment with the lateral branch opening can be difficult because the side catheter branch is spaced between the side balloon and the lateral branch opening of the stent. The stent structure (i.e. expandable struts of the stent) is typically too dense for the assembler to adequately visualize the side balloon through a sidewall of the stent for purposes of aligning the stent with the lateral branch opening. The assembler typically visualizes the side balloon through the lateral branch opening while making any axial and radial adjustments to the main catheter branch relative to the stent to provide alignment of the side balloon with the lateral branch opening. When the side catheter branch is extended through the lateral branch opening, the side catheter branch typically covers much of the side balloon from the assembler's view, making it difficult to confirm proper alignment of the side balloon relative to the lateral branch opening.

One aspect of the present disclosure relates to providing visualization of features of the side balloon or the side inflation member through the side catheter branch. An example feature that provides such visualization is providing at least that portion of the side catheter branch that overlaps the side balloon in a view through the lateral branch opening of the stent with a transparent material composition. The transparent material composition of that portion of the side catheter branch overlapping the side balloon permits visualizing by the assembler of the side balloon through the side catheter branch.

The side balloon can include one or more visual indicators that help the assembler better identify the side balloon when viewing the side balloon through the side catheter branch. Some example visual indicators for the side balloon include a marking (e.g., an "x", "+" or "o"), or a colorant that is different than the colorant of the side catheter branch, the main balloon, the side inflation member, or other features of the main catheter branch. Further examples and alternatives are described with reference to the attached Figures and description that follows.

Figure 1:
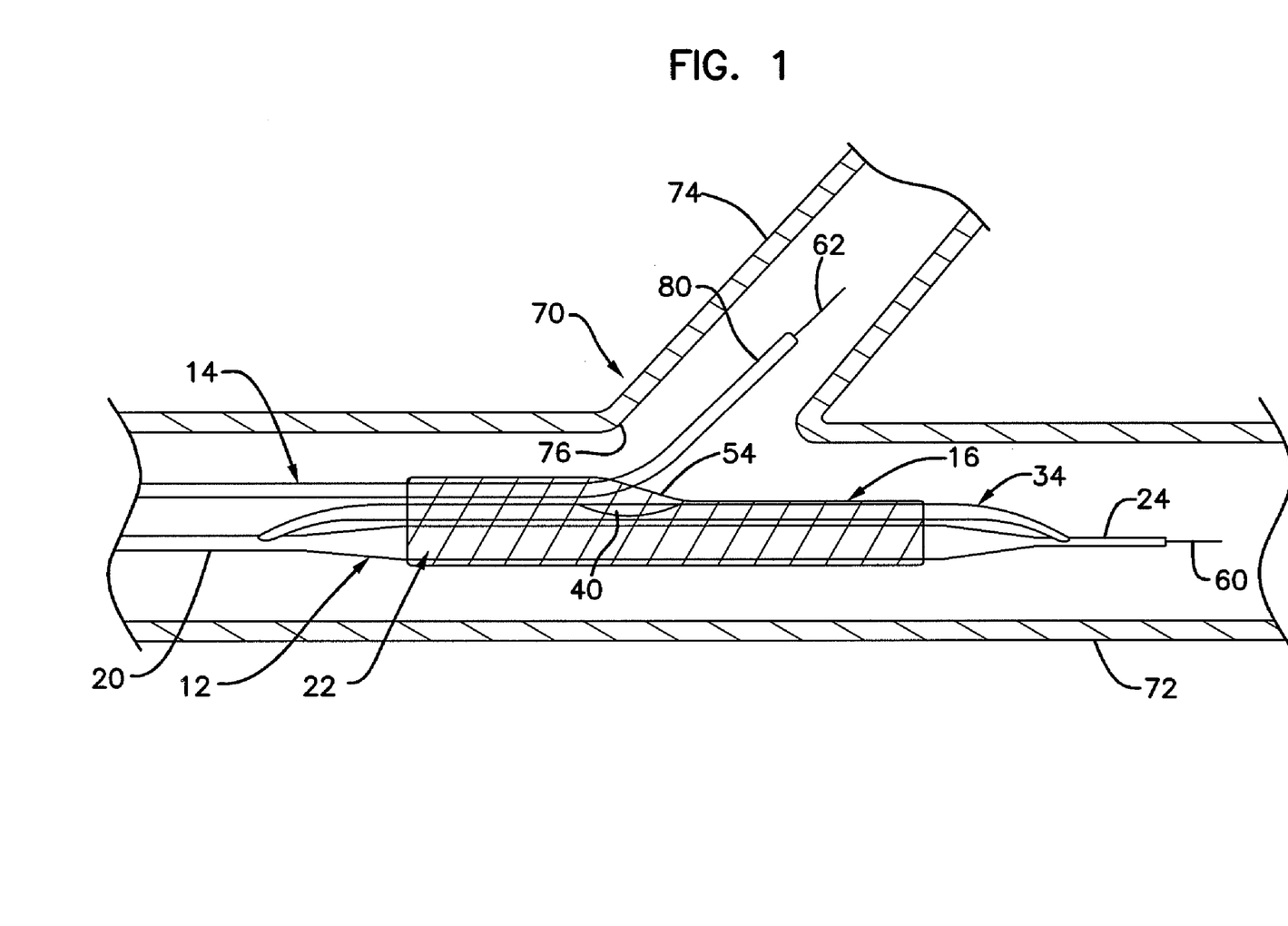
FIG. 1 is a schematic side view of an example catheter assembly in accordance with principles of the present disclosure, wherein the catheter assembly is positioned at a vessel bifurcation treatment site.
Figure 2:
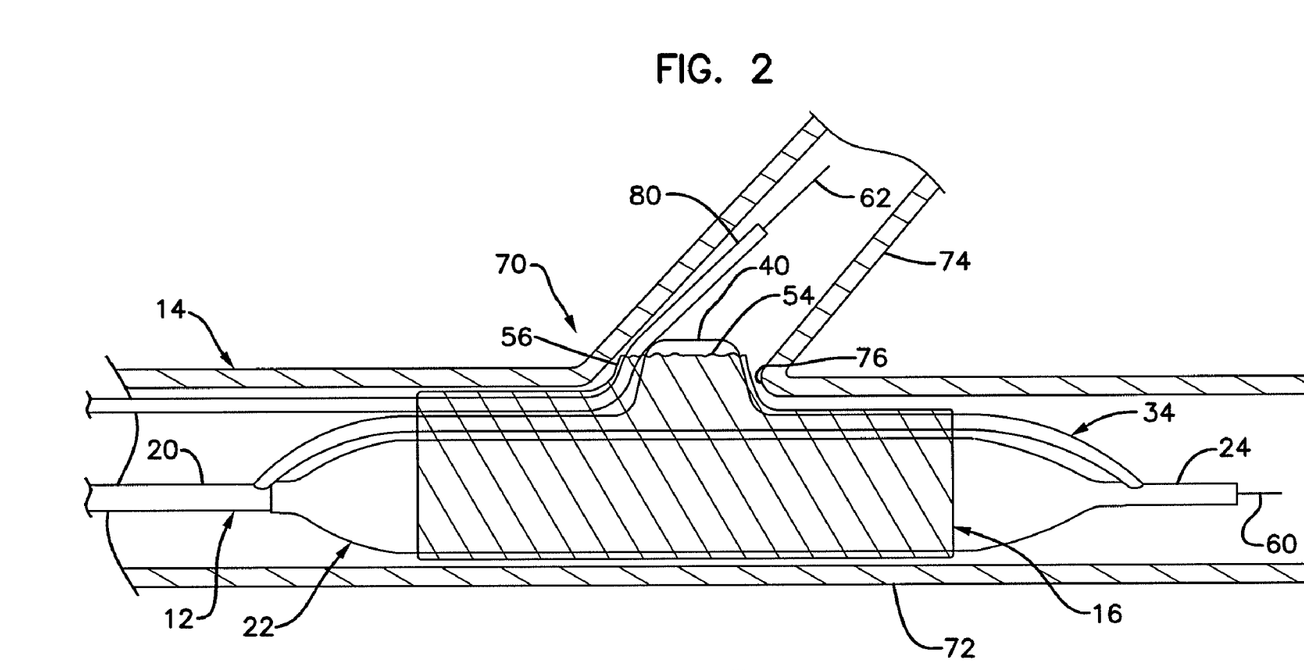
FIG. 2 is a schematic side view of the example catheter assembly shown in FIG. 1 with the catheter assembly treating the vessel bifurcation.

Referring now to FIGS. 1-2, an example catheter assembly 10 is shown and described with reference to treatment of a vessel bifurcation 70. The catheter assembly 10 includes a main catheter branch 12, a side catheter branch 14, and a stent 16. The main catheter branch 12 includes a catheter shaft 20, a main guidewire housing 24, a main balloon 22, a side inflation member 34, and a side balloon 40. The side catheter branch 14 has a distal end portion 80. The distal end portion 80 of the side catheter branch 14 extends through a lateral branch opening 84 of the stent 16. The lateral branch opening 84 is defined by a radially outward expandable portion 56 (see FIG. 7).

Figure 6:
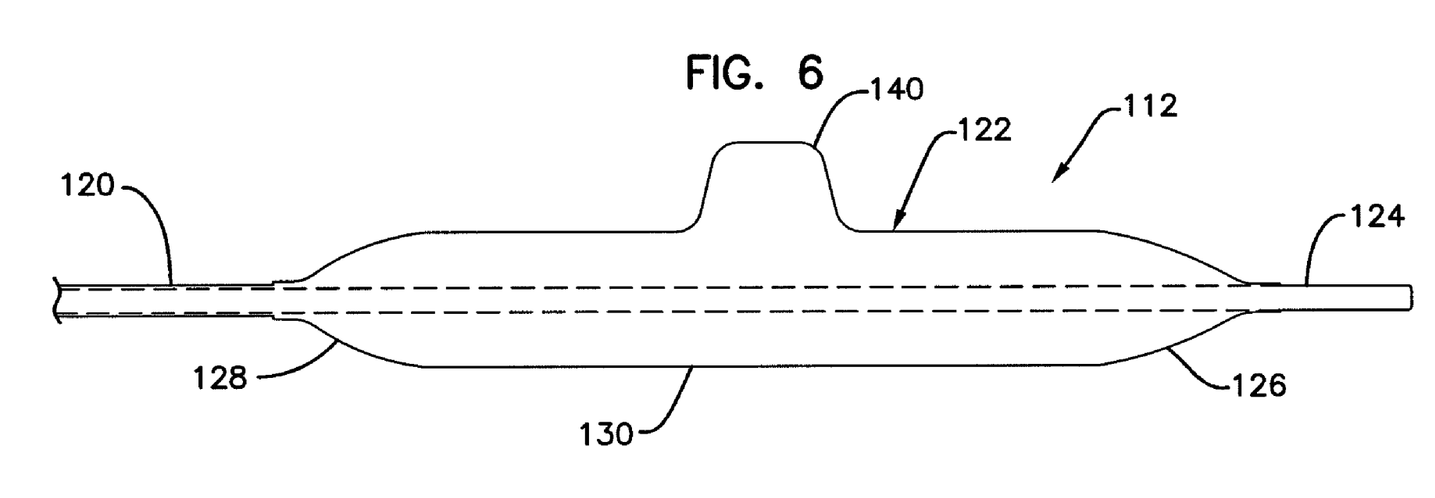
FIG. 6 is a schematic side view of the example main catheter branch shown in FIG. 5 with the main and side balloons in an inflated state.

While many other treatment methods and alternatives are possible, a method of treating a vessel bifurcation 70 can generally include the following. A main guidewire 60 is positioned in a main vessel 72 and a branch guidewire 62 is positioned in a branch vessel 74. The catheter assembly 10 is advanced over the main and branch guidewires 60, 62 to a location adjacent the vessel bifurcation 70 as shown in FIG. 6 with the distal end portion 80 of the side catheter branch 14 extending into the branch vessel 74. The catheter assembly 10 is adjusted radially and axially relative to the vessel bifurcation 70 until the lateral branch opening 54 of the stent 16 is aligned with an opening or ostium 76 into the branch vessel 74.

Figure 7:
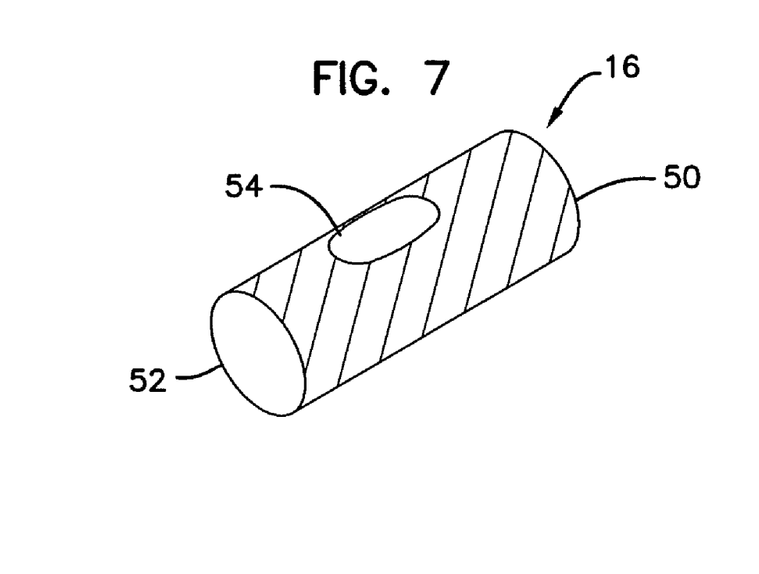
FIG. 7 is a schematic perspective view of an example stent for use with the catheter assembly shown in FIG. 1.

The main balloon 22 and side balloon 40 are then inflated to expand the stent into engagement with the main vessel 72 and expand the expandable portions 56 of stent 16 through the opening 76 and into the branch vessel 74 (see FIG. 7). Any misalignment of the side balloon 40 relative to the lateral branch opening 54 of the stent 16 resulting from incorrect assembly of catheter assembly 10 can result in improper expansion of the expandable portion 56 of stent 16 into the branch vessel 74.

After expansion of the stent 16, the main and side balloons 22, 40 are deflated and withdrawn proximally from the stent 16. Further treatment of the branch vessel 74 can be performed by advancing a post dilation balloon (not shown) through the lateral branch opening 54 and at least partially overlapping the expandable portions 84 and then inflating the post dilation balloon. A secondary stent can also be advanced into the branch vessel 74 and expanded while at least partially overlapping the expandable portions 56.

Figure 3:
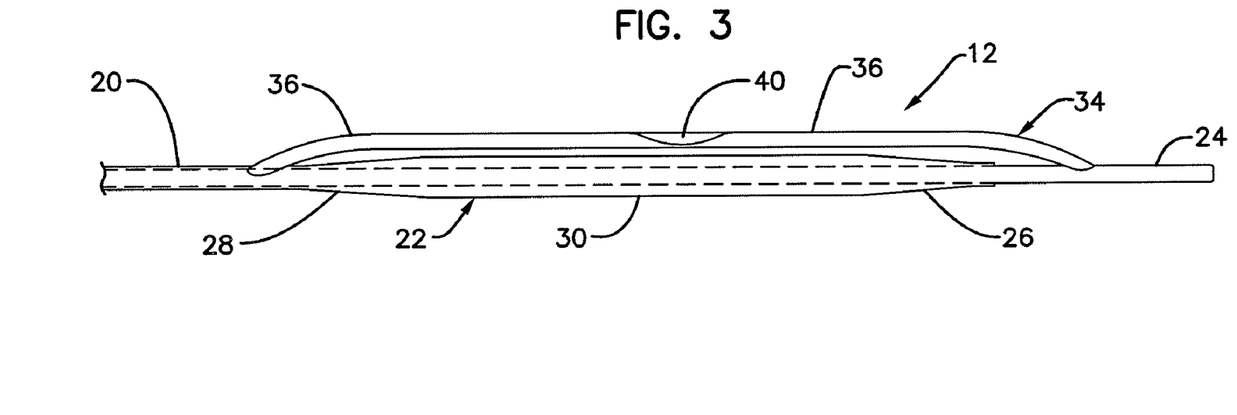
FIG. 3 is a schematic side view of an example catheter main branch for use in the catheter assembly shown in FIG. 1 with main and side balloons of the main catheter branch in a deflated state.
Figure 4:
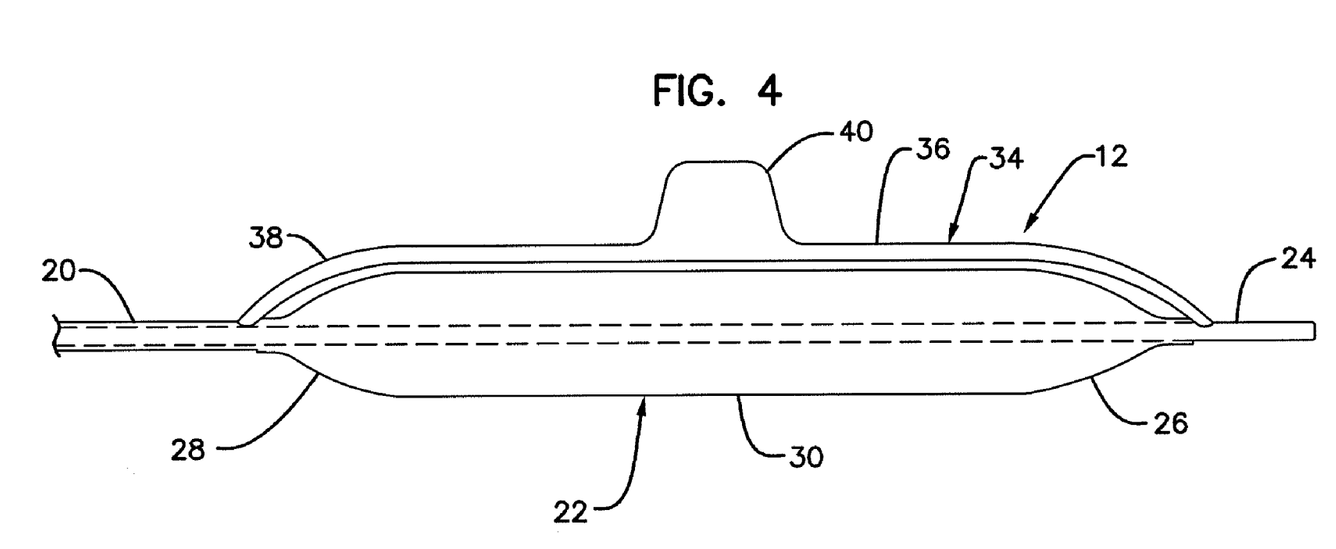
FIG. 4 is a schematic side view of the main catheter branch shown in FIG. 3 with the main and side balloons in an inflated state.

Referring now to FIGS. 3-4, the main catheter branch 12 shown in FIGS. 1 and 2 is described in further detail. The main balloon 22 includes distal and proximal end portions 26, 28 and a main body portion 30. While alternatives are possible, the main body portion 30 has a generally cylindrical shape with a circular cross section. The side inflation member 34 includes distal and proximal segments 36, 38 that intersect the side balloon 40 at distal and proximal sides of the side balloon 40, respectively. The distal segment 38 also typically intersects with the main guidewire housing 24 at a distal end of the distal segment 36. The proximal end 38 typically intersects with the catheter shaft 20 at a proximal end of the proximal segment 38. Although alternatives are possible, the side balloon 40 is typically arranged in fluid communication with the main balloon 22 via at least one of the distal and proximal segments 36, 38.

Figure 5:
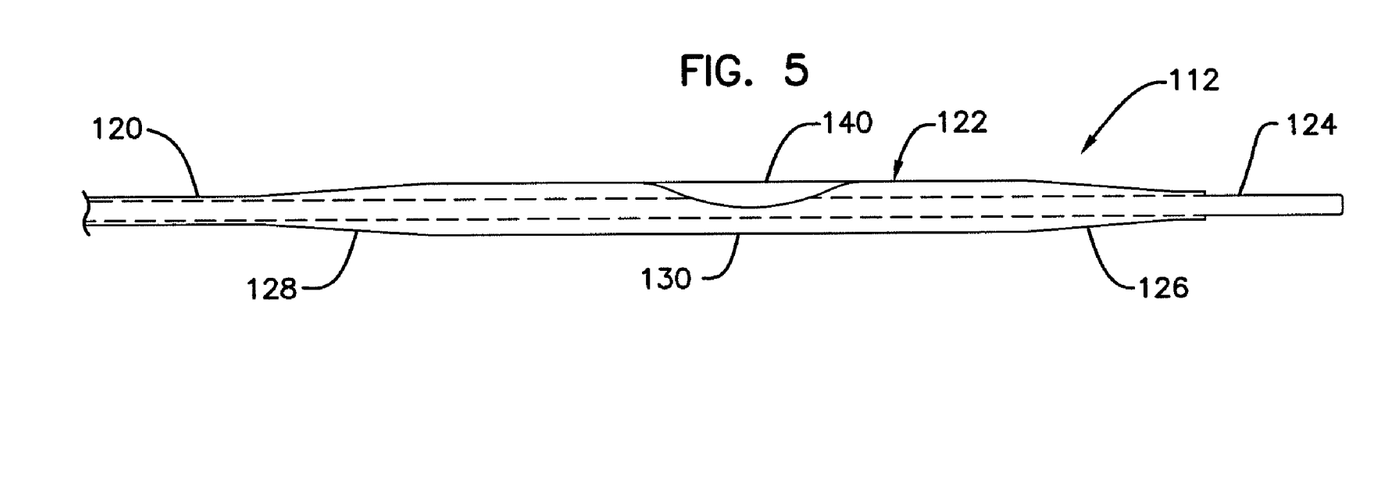
FIG. 5 is a schematic side view of another example main catheter branch for use with the catheter assembly shown in FIG. 1 with the main and side balloons in a deflated state.

In an alternative arrangement shown in FIGS. 5 and 6, a main catheter branch 112 includes a side balloon 140 positioned on the main balloon 122. The main catheter branch 112 includes a catheter shaft 120, a main balloon 122 having distal and proximal end portions 126, 128 and a body portion 130. The side balloon 140 is positioned at a location between the distal and proximal end portions 126, 128. The side balloon 140 can be integral with the main balloon 122. Alternatively, the side balloon 140 can be constructed as a separate piece that is connected or otherwise mounted to the main balloon 122 in a separate assembly step. Although alternatives are possible, the side balloon 140 is typically arranged in fluid communication with the main balloon 122. The main catheter branch 112 can provide the same or similar functionality as the main catheter branch 12 for purposes of expanding the stent 16 at a vessel bifurcation as described above with reference to FIGS. 1 and 2. The main catheter branches 12, 112 can be interchangeable for purposes of the inventive principles disclosed herein related to how features of a side catheter branch can influence alignment of the side balloon 40, 140 relative to a lateral branch opening of a stent.

FIG. 7 illustrates schematically an example perspective view of the stent 16. The stent 16 includes opposing distal and proximal open ends 50, 52, and a lateral branch opening 54 located at a position between the distal and proximal ends 50, 52. Typically, the stent 16 would include a plurality of struts that define the generally cylindrical side wall construction of the stent 16. An additional set of struts of the stent define the lateral branch opening 54 and are configured to extend in a radially outward orientation (e.g., see FIG. 2) upon inflation of the side balloon 40, 140. Further details concerning example stent constructions for use with the catheter assembly 10 are described in further detail below.

Figure 8:
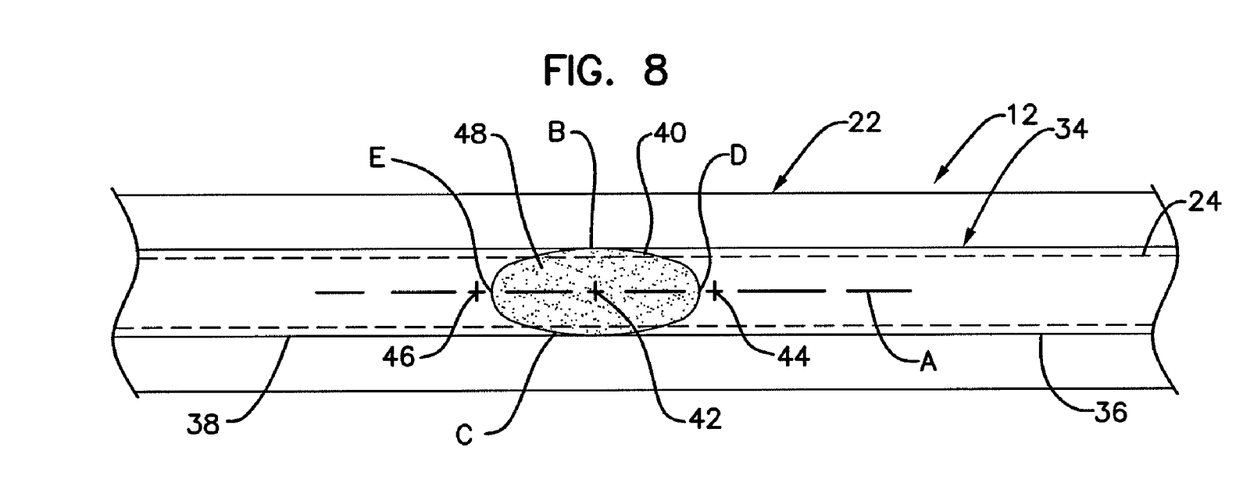
FIG. 8 is a schematic partial top view of the main branch shown in FIG. 3.

FIG. 8 illustrates a top view of a portion of the main catheter branch 12. The side balloon 40 is positioned along the side inflation member 34. The side balloon 40 can include any one of a plurality of different visual indicators such as, for example, a colorant 48 or a marker 42. The colorant 48 can be included in all of the side balloon 40 or only in a portion of the side balloon 40. The colorant 48 can have a contrasting color to the color of the distal and proximal segments 36, 38 of the inflation member 34, the main balloon 22, and the main guidewire housing 24. In one example arrangement, at least the main balloon 22 and inflation member 34 comprise no colorants and are substantially transparent, and the main guidewire housing 24 comprises a colorant (e.g., a green colorant that is substantially non-transparent) while the side balloon 40 comprises a colorant 48 that is different from the colorant of the main guidewire housing 24.

A marker 42 can be positioned on the side balloon 40 in place of or in combination with the colorant 48. Although alternatives are possible, the marker 42 generally is provided centrally on the side balloon 40, such as along a central proximal-distal line that extends from a distal most point D to a proximal most point E on the side balloon 40 (e.g., line A shown in FIG. 8), wherein the central line A is centrally located between lateral sides B and C of side balloon 40 (see FIG. 8). The marker 42 can comprise any shape, size, and arrangement of one or more markers. Some example shapes include a +, x, ○, or □ shape. The marker 42 can include two or more markers that help identify different features of the side balloon 40 such as, for example, a central point along the central line A or distal and/or proximal points on the balloon 40.

One or more additional markers 44, 46 can be positioned on the side inflation member 34 in place of or in combination with the marker 42 and colorant 48 of the side balloon 40. FIG. 8 illustrates a distal marker 44 positioned on the side inflation member 34 at a location distal of and adjacent to the side balloon 40. A proximal marker 46 is positioned on the side inflation member 34 at a location proximal of and adjacent to a proximal side of the side balloon 40. Any number, size, shape and arrangement of markers 44, 46 (e.g., the example shapes and size and numbers of markers as described above with relation to marker 42) can be used on the side inflation member 34. Typically, the markers and colorants 42, 44, 46, 48 are visually perceptible to an assembler of catheter assembly 10 when viewing the main catheter branch 12 through at least a portion of the lateral branch opening 54 of the stent 16.

Figure 9:
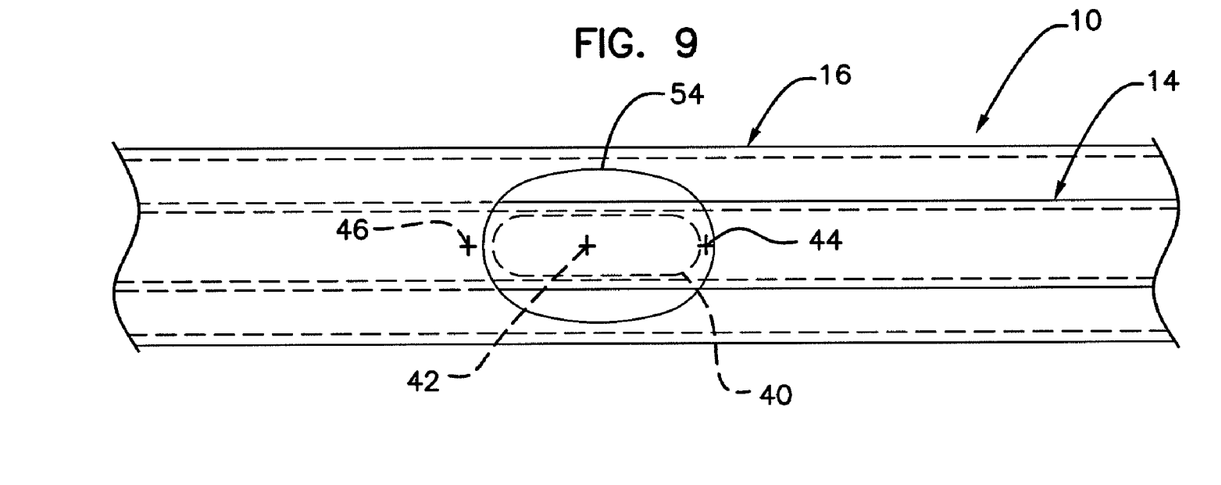
FIG. 9 is a schematic partial top view of the catheter assembly shown in FIG. 1.

FIG. 9 illustrates a portion of the catheter assembly 10 from a top view. The main catheter branch 12 is positioned within stent 16 and the side catheter branch 14 extends through the lateral branch opening 54 of stent 16. The side catheter branch 14 can substantially cover the side balloon 40 from an assembler's view in this arrangement. In configurations in which the side catheter branch 14 comprises a substantially non-transparent material composition, those portions of the side balloon 40 that are overlapped by the side catheter branch 14 can be substantially shielded from the assembler's view. Providing the side catheter branch 14 with a transparent material in at least that area of the side catheter branch 14 that overlaps the side balloon 40 (i.e., in the area of lateral branch opening 54), can permit the assembler to visualize the side balloon 40 or at least aspects of the side balloon 40 such as, for example, the marker 42, the colorant 48, or markers 44, 46 of the side inflation member 34 that are helpful to visualize for purposes of aligning the side balloon 40 with the lateral branch opening 54.

While alternates are possible, FIGS. 10-13 illustrate several example side catheter branch configurations that provide the desired transparency for visualizing aspects of the main catheter branch 12 such as the side balloon 40. The side catheter branch configurations shown and described with reference to FIGS. 10-13 can be used in place of the side catheter branch 14 described herein.

Figure 10:
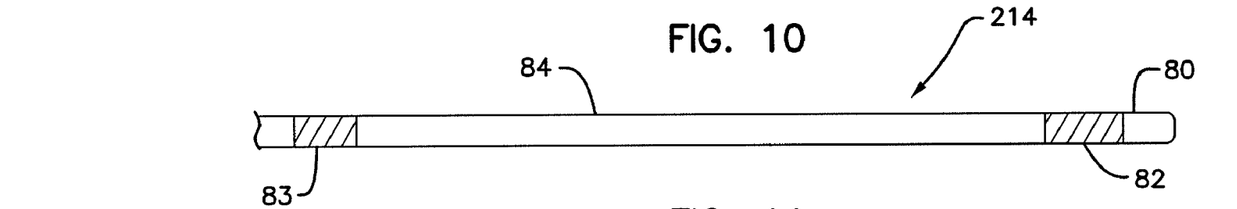
FIG. 10 is a schematic side view of a portion of an example side branch for use with the catheter assembly shown in FIG. 1.

FIG. 10 illustrates a side catheter branch 214 that includes a transparent portion 84 that extends along substantially an entire length of the side catheter branch 214. Because the transparent portion 84 extends along substantially all the length of the side catheter branch 214, an axial position of the side catheter branch 214 relative to the side balloon 40 is not critical to provide desired visualization of the side balloon 40.

A side catheter branch 214 that is transparent along substantially its entire length can result in challenges in handling the side catheter branch 214 during assembly of the catheter assembly 10. The side catheter branch 214 is relatively small as are the features of the main catheter branch 12 and stent 16. Providing some type of marker or other visual indicator along the length of the side catheter branch 214, particularly at or near the distal end portion 80, can help the assembler identify the side catheter branch 214 easier during assembly of the catheter assembly 10. One or more markers 82, 83 can be positioned on the side catheter branch 214 to provide such visual indicators. The markers 82, 83 can be constructed of material that is visible while the side catheter branch 214 is positioned within the patient using, for example, fluoroscopy or other technology. In some arrangements, the use of markers that are visible under fluoroscopy will add to the outer profile of the catheter assembly 10 because such markers comprise a metal material such as gold or tungsten that is resistant to deformation when compressed (e.g., when the stent is crimped).

The markers 82, 83 can have multiple purposes. For example, in addition to providing visualization of the side catheter branch 214 during assembly of the catheter assembly 10, the markers 82, 83 can indicate movement of the distal end portion 80 into a branch vessel at the vessel bifurcation when treating the vessel bifurcation.

Figure 11:
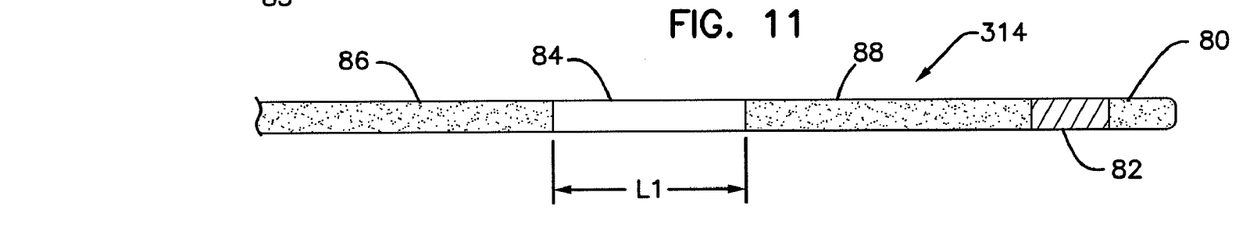
FIG. 11 is a schematic side view of a portion of another example side branch for use with the catheter assembly shown in FIG. 1.

FIG. 11 illustrates another example side catheter branch 314 that includes a transparent portion 84, a proximal non-transparent portion 86, and a distal non-transparent portion 88. The transparent portion 84 is located along the side catheter branch 314 at a position that substantially overlaps axially with the position of the side balloon of the main catheter branch 12. The non-transparent portions 86, 88 can provide visualization of the side catheter branch 314 for purposes of handling of the side catheter branch 314 during assembly of the catheter assembly 10. The side catheter branch 314 can also include a marker 82 that is visible from within the patient's body using, for example, fluoroscopy as described above. A length L1 of the transparent portion 84 can vary depending on, for example, the size of the side balloon 40, the size of the lateral branch opening 54, and the size or location of any visual indicators positioned on the side balloon 40 or side inflation member 34.

Figure 12:
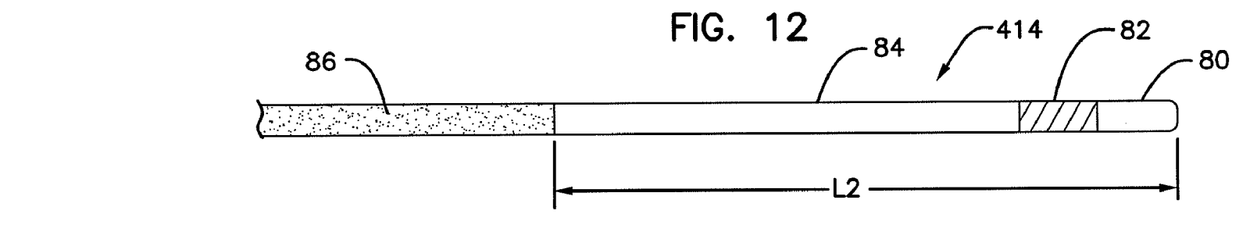
FIG. 12 is a schematic side view of a portion of another example side branch for use with the catheter assembly shown in FIG. 1.

FIG. 12 illustrates another example side catheter branch 414 that includes a transparent portion 84, a non-transparent portion 86 and a marker 82. The transparent portion 84 extends from a distal end at the distal end portion 80 proximally to a position of the side balloon 40 of the main catheter branch 12 when the catheter assembly 10 is assembled. The transparent portion 84 can terminate at a proximal location spaced a distance L2 from a distal end of the side catheter branch 414 at a location proximal to any visual indicators on the side balloon 40 that are used to align the side balloon 40 with the lateral branch opening 54 of the stent 16.

Figure 13:
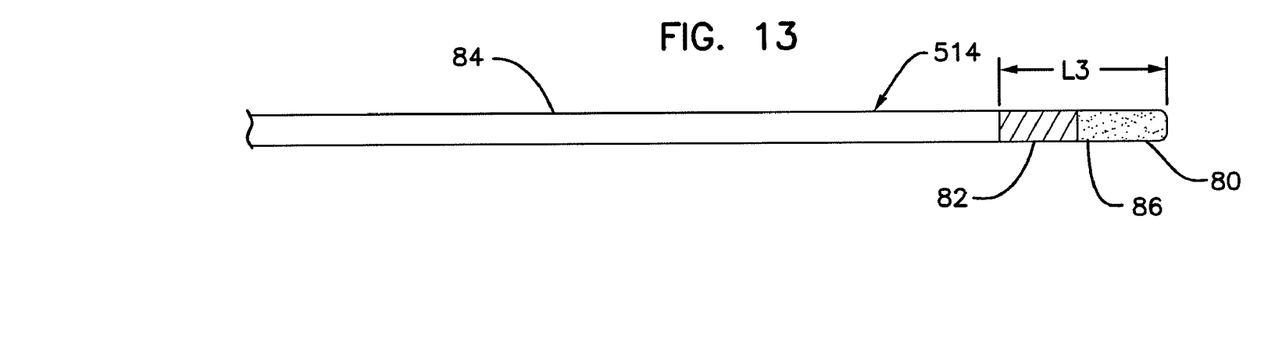
FIG. 13 is a schematic side view of a portion of another example side branch for use with the catheter assembly shown in FIG. 1.

FIG. 13 illustrates a still further example side catheter branch 514. The side catheter branch 514 includes a transparent portion 84, a non-transparent portion 86, and a marker 82. The non-transparent portion 86 is positioned at the distal end portion 80 of the side catheter branch 514. The non-transparent portion 86 can have a relatively short length L3 while being sufficiently long to provide a visual indicator of the side catheter branch 514 for improved ease in handling the side catheter branch 514 by the assembler. The transparent portion 84 extends along at least that portion of the side catheter branch 514 that overlaps axially with the side balloon 40 or any visual indicators on the side balloon or the side inflation member 34 that would be helpful in aligning the side balloon 40 with the lateral branch opening 54 of the stent 16.

Materials and Other Considerations

The term "transparent" as used herein for purposes of describing a portion of a side catheter branch is defined as a structure through which a visual indicator of the main catheter branch can be identified by an assembler. A transparent structure typically has properties of transmitting light without appreciable scattering so that bodies lying beyond the side catheter branch are visible. Alternatively, the term "transparent" can be defined as a structure that is fine or sheer enough to be seen through. The term "transparent" as it applies to the side catheter branch features disclosed herein can be at least partially translucent in which a certain amount of light is able to pass through the side catheter branch so that objects beyond the translucent structure, while not clearly seen, can be seen well enough to identify the visual indicator on the main catheter branch to provide the assembler the ability to properly align the side balloon with the lateral branch opening of the stent. In some cases, visibility of the assembler can be enhanced with the use of magnifying equipment such as a magnifying glass or a microscope, thermal equipment, or emissive equipment depending on the properties of the visual indicator on the main catheter branch.

A wide variety of stents, catheters, and guidewire configurations can be used with the catheter assembly embodiments of the present disclosure. The inventive principles disclosed herein should not be limited to any particular design or configuration. Some example stents that can be used with the catheter assemblies disclosed herein can be found in, for example, U.S. Pat. Nos. 6,210,429, 6,325,826 and 6,706,062, 7,220,275 to Vardi et al., and U.S. Published Patent Application No. 2004/0176837 titled SELF-EXPANDING STENT AND CATHETER ASSEMBLY AND METHOD FOR TREATING BIFURCATIONS, the entire contents of which are incorporated herein by reference. In general, the aforementioned stents include a lateral branch opening located between distal and proximal open ends of the stent. The lateral branch opening defines a path between an inner lumen or inner volume of the stent and an area outside of the stent. The stent lateral branch opening is distinct from the cell openings defined between strut structures from which the stent sidewall is constructed. In some stents, the lateral branch opening can be surrounded by expandable structure. The expandable structure can be configured to extend radially into the branch lumen of the bifurcation upon expansion of, for example, an inflatable portion of the bifurcation treatment system. Typically, the stent is expanded after being positioned in the main lumen with the lateral branch opening aligned with an opening into the branch lumen. Alignment of the lateral branch opening with the opening into the branch lumen includes both radial and axial alignment. The stent, including the expandable structure surrounding the lateral branch opening, can be expanded with a single expansion or multiple expansions using one or more inflatable members.

The main and side balloons, and all other balloons disclosed herein, can be made of any suitable balloon material including compliant and non-compliant materials and combinations thereof. Some example materials for the balloons and catheters disclosed herein include thermoplastic polymers, polyethylene (high density, low density, intermediate density, linear low density), various copolymers and blends of polyethylene, ionomers, polyesters, polycarbonates, polyamides, poly-vinyl chloride, acrylonitrile-butadiene-styrene copolymers, polyether-polyester copolymers, and polyether-polyamide copolymers. One suitable material is Surlyn®, a copolymer polyolefin material (DuPont de Nemours, Wilmington, Del.). Still further suitable materials include thermoplastic polymers and thermoset polymeric materials, poly (ethylene terephthalate) (commonly referred to as PET), thermoplastic polyamide, polyphenylene sulfides, polypropylene. Some other example materials include polyurethanes and block copolymers, such as polyamide-polyether block copolymers or amide-tetramethylene glycol copolymers. Additional examples include the PEBAX® (a polyamide/polyether/polyester block copolymer) family of polymers, e.g., PEBAX® 70D, 72D, 2533, 5533, 6333, 7033, or 7233 (available from Elf AtoChem, Philadelphia, Pa.). Other examples include nylons, such as aliphatic nylons, for example, Vestamid L2101 1F, Nylon 11 (Elf Atochem), Nylon 6 (Allied Signal), Nylon 6/10 (BASF), Nylon 6/12 (Ashley Polymers), or Nylon 12. Additional examples of nylons include aromatic nylons, such as Grivory (EMS) and Nylon MXD-6. Other nylons and/or combinations of nylons can also be used. Still further examples include polybutylene terephthalate (PBT), such as CELANEX® (available from Ticona, Summit, N.J.), polyester/ether block copolymers such as ARNITEL® (available from DSM, Erionspilla, Ind.), e.g., ARNITEL® EM740, aromatic amides such as Trogamid (PA6-3-T, Degussa), and thermoplastic elastomers such as HYTREL® (Dupont de Nemours, Wilmington, Del.). In some embodiments, the PEBAX®, HYTREL®, and ARNITEL® materials have a Shore D hardness of about 45D to about 82D. The balloon materials can be used pure or as blends. For example, a blend may include a PBT and one or more PBT thermoplastic elastomers, such as RITEFLEX® (available from Ticona), ARNITEL®, or HYTREL®, or polyethylene terephthalate (PET) and a thermoplastic elastomer, such as a PBT thermoplastic elastomer. Additional examples of balloon material can be found in U.S. Pat. No. 6,146,356, which is incorporated herein by reference.

The catheter assembly 10 can include marker material that is visible under X-ray or in fluoroscopy procedures. For example, the marker material can be more easily identified and distinguished under X-ray or in fluoroscopy procedures. Some example marker materials include gold, platinum and tungsten. In one embodiment, the marker material can be included in a band structure that is secured to the side catheter branch 14. In other embodiments, the marker material is part of the material composition of portions of the side catheter branch 14. Viewability of features of the catheter assembly 10 under X-ray or fluoroscopy can assist a physician operating the catheter assembly 10 to more easily adjust a position of the assembly 10 relative to the vessel bifurcation 70. Example markers and marker materials suitable for use with assembly 10 are described in, for example, U.S. Pat. No. 6,692,483 to Vardi, et al., and co-pending U.S. Published Patent Application No. 2007/0203562, filed on Feb. 22, 2007, and titled MARKER ARRANGEMENT FOR BIFURCATION CATHETER, which matters are incorporated herein by reference.

Alternative catheter assemblies to those described above are configured for use with stents having self-expanding features. Self-expanding stents and self-expanding features of a stent typically do not require the use of an inflatable member such as a balloon to expand the sent or stent feature. Typically, self-expanding stents, such as those stents described in U.S. Published Patent Application No. 2004/0176837, are held in a constricted state using a sheath that fits over the stent. In the constricted state, the stent is able to navigate through a body lumen to the treatment site. Once the stent and sheath are positioned at the treatment side, the sheath is retracted proximally to release the stent for expansion of the stent into a radially expanded state.

One aspect of the present disclosure relates to a catheter assembly that includes a stent, a main catheter branch, and a side catheter branch. The stent has a proximal open end, a distal open end, and a lateral branch opening. The main catheter branch includes a proximal end portion and a distal end portion, wherein the distal end portion includes a main balloon and a side balloon. The main balloon has a proximal end portion, a distal end portion, and a cylindrical body portion extending between the proximal and distal end portions. The side balloon is arranged at a location between the proximal and distal end portions of the main balloon. The side balloon is configured to extend radially outward relative to the main balloon when the side balloon is inflated. The side balloon also defines a central proximal-distal line. The side catheter branch defines a branch guidewire lumen and extends through the lateral branch opening of the stent. The side catheter branch comprises a transparent portion along a length of the side catheter branch. The transparent portion permits visualization through the side catheter branch to align the side balloon with the lateral branch opening of the stent.

Another aspect of the present disclosure relates to a catheter assembly that includes a main balloon, a side balloon, and a side catheter branch. The main balloon has a proximal end portion, a distal end portion, and a cylindrical body portion extending from the proximal end portion to the distal end portion. The side balloon is positioned at a location between the proximal and distal end portions of the main balloon. The side balloon is configured to extend radially outward relative to the main balloon when the side balloon is inflated. The side catheter branch defines a branch guidewire lumen and includes a transparent portion. The transparent portion permits visualization through the side catheter branch for alignment of the side catheter branch with the side balloon.

A still further aspect of the present disclosure relates to a method of assembling a catheter assembly. The catheter assembly includes a stent, a main catheter branch, and a side catheter branch. The stent has a proximal open end, a distal open end, and a lateral branch opening. The main catheter branch includes a main balloon, and a side balloon, wherein the side balloon is configured to extend radially outward relative to the main balloon when the side balloon is inflated. The side catheter branch defines a branch guidewire lumen, and the side catheter branch includes a transparent portion. The method steps include extending the main catheter branch into the stent with the main balloon and the side balloon positioned in the stent, extending the side catheter branch into the stent with the side catheter branch extending through the later branch opening of the stent, and viewing the side balloon through the transparent portion of the side catheter branch to align the side balloon with the lateral branch opening and with the side catheter branch.

It is noted that not all of the features characterized herein need to be incorporated within a given arrangement, for the arrangement to include improvements according to the present disclosure.

We claim:

1. A catheter assembly, comprising:
   (a) a stent having a proximal open end, a distal open end, and a lateral branch opening;
   (b) a main catheter branch having a proximal end portion and a distal end portion, the distal end portion including:
      i. a main balloon, the main balloon having a proximal end portion, a distal end portion, and a cylindrical body portion extending between the proximal and distal end portions; and
      ii. a side balloon arranged at a location between the proximal and distal end portions of the main balloon, the side balloon configured to extend radially outward relative to the main balloon when the side balloon is inflated, the side balloon defining a central proximal-distal line; and
   (c) a side catheter branch defining a branch guidewire lumen, the side catheter branch extending through the lateral branch opening of the stent, the side catheter branch comprising a transparent portion extending through the lateral branch opening of the stent and to a distal end of the side catheter branch, the transparent portion extending adjacent to and overlapping the side balloon, the transparent portion permitting visualization of the side balloon through the side catheter branch to align the side balloon with the lateral branch opening of the stent, the side catheter branch further comprising a non-transparent portion or a marker permitting visualization of the side catheter branch.

2. The assembly of claim 1, wherein the transparent portion of the side catheter branch extends around a circumference of the side catheter branch.

3. The assembly of claim 1, wherein the marker includes at least one marker band positioned along the side catheter branch.

4. The assembly of claim 1, wherein a distal end portion of the side catheter branch arranged distal of the side balloon includes the non-transparent material.

5. The assembly of claim 4, wherein the side balloon comprises a material having a colorant, and the non-transparent material of the side catheter branch includes a colorant that is different from the colorant of the side balloon.

6. The assembly of claim 1, wherein the side balloon includes a visual indicator that is visible through the transparent portion of the side catheter branch.

7. A catheter assembly, comprising:
(a) a main balloon, the main balloon having a proximal end portion, a distal end portion, and a cylindrical body portion extending from the proximal end portion to the distal end portion;
(b) a side balloon positioned at a location between the proximal and distal end portions of the main balloon, the side balloon configured to extend radially outward relative to the main balloon when the side balloon is inflated; and
(c) a side catheter branch defining a branch guidewire lumen, the side catheter branch having a transparent portion and a non-transparent portion, the transparent portion extending along and adjacent to the side balloon permitting visualization of the side balloon through the side catheter branch for alignment of the side catheter branch with the side balloon.

8. The assembly of claim 7, wherein a distal end portion of the side catheter branch arranged distal of the side balloon includes the non-transparent material.

9. The assembly of claim 8, wherein the side balloon comprises a material having a colorant, and the non-transparent material of the side catheter branch includes a colorant that is different from the colorant of the side balloon.

10. The assembly of claim 7, wherein the side balloon includes a visual indicator that is visible through the transparent portion of the side catheter branch.

11. The assembly of claim 10, wherein the visual indicator is positioned on an exterior surface of the side balloon.

12. The assembly of claim 10, wherein the visual indicator is selected from plus (+), cross (x), circular (○), or square (□) shape.

13. The assembly of claim 7, further comprising a stent, the stent having a proximal open end, a distal open end, and a lateral branch opening, wherein the side balloon is positioned within the stent and is visible through the transparent portion of the side catheter branch to align the side balloon with the lateral branch opening.

14. The assembly of claim 7, further comprising a main guidewire member that extends through the main balloon, the main guidewire member defining a main guidewire lumen sized to advance over a main guidewire.

15. A catheter assembly, comprising:
a main catheter branch having a proximal end portion and a distal end portion, the main catheter branch defining a main guidewire housing that is substantially non-transparent;
a main balloon having a proximal end portion, a distal end portion, and a cylindrical body portion extending between the proximal and distal end portions, the main balloon provided around the distal end portion of the main catheter branch such that the main guidewire housing extends through the main balloon;
a side balloon positioned adjacent to the main balloon and configured to extend radially outward relative to the main balloon when the side balloon is inflated, the side balloon comprising a side balloon marker; and
a side catheter branch defining a branch guidewire lumen, the side catheter branch including a transparent portion along a length of the side catheter branch extending adjacent to and overlapping the side balloon to permit visualization of the side balloon through the side catheter branch, wherein the side balloon marker is visible through the transparent portion of the side catheter branch.

16. The catheter assembly of claim 15, further comprising a stent having a proximal open end, a distal open end, and a lateral branch opening, wherein the side catheter branch extends through the lateral branch opening of the stent, and the transparent portion of the side catheter branch permitting visualization through the side catheter branch to align the side balloon with the lateral branch opening of the stent.

17. The catheter assembly of claim 15, wherein the side catheter branch includes a non-transparent portion positioned distal of the side balloon.

18. The catheter assembly of claim 15, wherein the side catheter branch includes at least one marker positioned along a length of the side catheter branch.

* * * * *